(12) United States Patent
Waldstein

(10) Patent No.: US 8,715,581 B2
(45) Date of Patent: May 6, 2014

(54) MODULAR POWER PLANT UNCONNECTED TO THE GRID

(75) Inventor: Gregor Waldstein, Salzburg (AT)

(73) Assignee: SolarFuel GmbH, Stuttgart (DE)

( * ) Notice: Subject to any disclaimer, the term of this patent is extended or adjusted under 35 U.S.C. 154(b) by 659 days.

(21) Appl. No.: 12/744,104

(22) PCT Filed: Nov. 20, 2008

(86) PCT No.: PCT/EP2008/009803
§ 371 (c)(1),
(2), (4) Date: May 16, 2011

(87) PCT Pub. No.: WO2009/065577
PCT Pub. Date: May 28, 2009

(65) Prior Publication Data
US 2011/0237839 A1    Sep. 29, 2011

(30) Foreign Application Priority Data
Nov. 22, 2007 (CH) .................................. A 1807/07

(51) Int. Cl.
*B01J 8/00* (2006.01)
*B01J 19/00* (2006.01)
*F03G 6/00* (2006.01)
*F03G 7/00* (2006.01)
*F01K 27/00* (2006.01)

(52) U.S. Cl.
USPC ..... 422/187; 422/129; 60/641.11; 60/641.12; 60/641.13; 60/641.14; 60/641.15; 60/641.1; 60/641.2; 60/641.9

(58) Field of Classification Search
USPC ........ 422/129, 187; 60/60, 495, 641.1, 641.2, 60/641.9, 641.11–641.15
See application file for complete search history.

(56) References Cited

U.S. PATENT DOCUMENTS 3,852,180 A * 12/1974 Gregory ........................ 204/277
4,085,795 A    4/1978 Gill (Continued)

FOREIGN PATENT DOCUMENTS

DE    3933284    4/1991
DE    4235125    4/1994

(Continued)

OTHER PUBLICATIONS

Machine translation of DE 4332789 A1, provided in IDS filed May 21, 2010 and published on Mar. 30, 1995.*

(Continued)

*Primary Examiner* — Natasha Young
(74) *Attorney, Agent, or Firm* — Cooper & Dunham LLP

(57) ABSTRACT

The invention relates to a grid-connected power plant, having the following systems which are adjusted in their capacitance to each other: a) a wind power plant, water power plant, solar-thermal system and/or photovoltaic system for the production of electrical energy for operating the systems b) through f); b) a CO2 absorption system for the absorption of atmospheric CO2; c) a CO2 desorption system for the desorption of the CO2 gained in b); d) an electrochemical or solar-thermal H2 synthesis system for the operating system e); e) a synthesis system selected from the group catalytic methanol synthesis, catalytic DME synthesis, catalytic methane synthesis; f) a storage system selected from the group methanol storage system, DME storage system, methane storage system. The invention also relates to the use of such a power plant and methods for the operation of such a power plant.

13 Claims, 3 Drawing Sheets

(56) References Cited

U.S. PATENT DOCUMENTS

Figure 1:
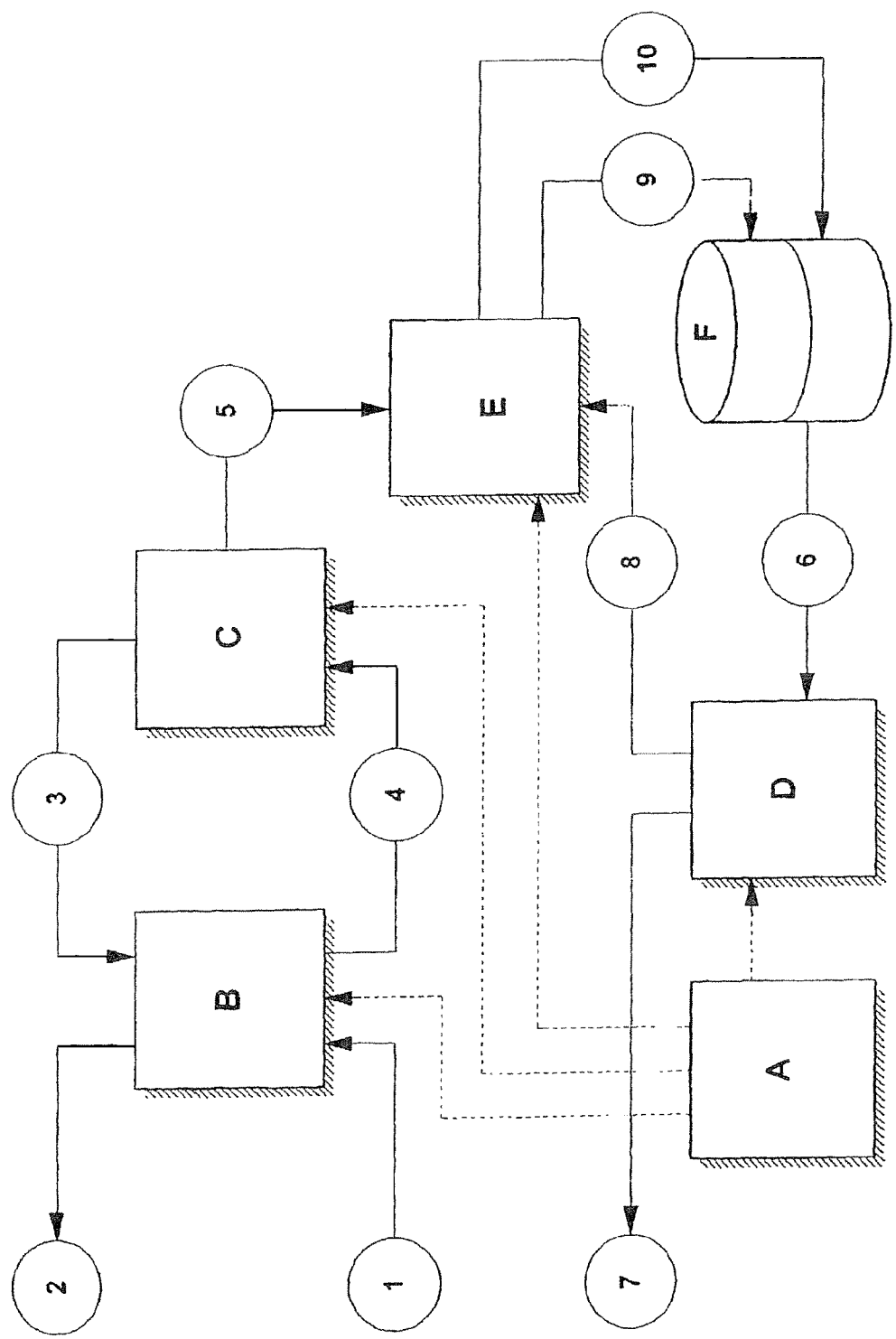

| | | | |
|---|---|---|---|
| 4,341,069 A * | 7/1982 | Bell et al. | 60/781 |
| 4,627,418 A | 12/1986 | Gibson et al. | |
| 5,246,551 A | 9/1993 | Pletcher et al. | |
| 5,772,791 A * | 6/1998 | Laing | 136/246 |
| 7,318,854 B2 * | 1/2008 | Sirkar | 95/45 |
| 2003/0168864 A1 * | 9/2003 | Heronemus et al. | 290/55 |
| 2010/0005966 A1 * | 1/2010 | Wibberley | 95/179 |
| 2010/0205856 A1 | 8/2010 | Kubic et al. | |

FOREIGN PATENT DOCUMENTS

| | | |
|---|---|---|
| DE | 4332789 | 3/1995 |
| DE | 19802660 | 7/1999 |
| WO | WO 9316216 | 8/1993 |
| WO | WO 00/25380 | 5/2000 |
| WO | WO 2005/056737 | 6/2005 |
| WO | WO 2007/058608 | 5/2007 |
| WO | WO 2009048685 | 4/2009 |

OTHER PUBLICATIONS

S. Stucki et al., Jan. 10, 1995, "Coupled $CO_2$ Recovery from the Atmosphere and Water Electrolysis: Feasibility of a New Process for Hydrogen Storage", vol. 20, No. 8, pp. 653-663.

International Search Report in corresponding PCT/EP2008/009803 dated Apr. 20, 2009.

* cited by examiner

MODULAR POWER PLANT UNCONNECTED TO THE GRID

The invention relates to a power plant, which is not connected to the grid and produces and stores hydrocarbons from carbon dioxide of the air, water and regenerative energy, these power plants preferably being installed on a floating body. Furthermore, the invention relates to the use of such a power plant and to methods for operating such a power plant.

There is a general need for making energy available inexpensively and environmentally neutral. At the present time, fossil energy carriers supply the bulk of the global energy. However, the use of these energy carriers is limited by the existing reserves and by the tolerance of world climate for emissions of the combustion product CO2. Because of the unsolved disposal question, nuclear energy is rejected by responsible decision makers. Furthermore, general solutions are known for making electrical energy available from renewable sources of energy. Furthermore, solutions are known for producing liquid fuels from biomass. Biogenic fuels use the chemical energy formed from CO2 and H2O by photosynthesis and stored in biomass and form a portion of a closed material cycle. However, the use of biomass for supplying energy is in conflict with the use of biomass for nutrition and other purposes (biodiversity/living space). That part of the surface of the earth, on which conditions suitable for photosynthesis exist, is small and can hardly be expanded. With present (BTL) technologies, about 20% of the global photosynthesis capacity would have to be used for energy purposes. Even the slight contribution provided by biomass at the present time already has massive undesirable effects on the agricultural market. Energy from the sun and from wind is available only in low densities and not according to need. These forms of energy can therefore make a substantial contribution to the global supply of energy only if they can be "harvested" and stored meaningfully over a large area. At the present time, both forms of energy can be used only, if they are stationary or connected with the consumer ("connected to the grid"). As a result, the choice of locations is greatly limited. Suitable storage systems of the energy generated, which permit storage and transport over large distances, are lacking.

Furthermore, it is a disadvantage of the known methods that storage media for electric energy have a low energy density; furthermore, the renewable energies frequently can be generated advantageously at places and/or times, at which the demand is only slight. On the other hand, liquid energy carriers, especially hydrocarbons, can be stored and transported easily and have a high energy density. Furthermore, a mature infrastructure exists for these energy carriers. In this connection, methanol must be mentioned as a particularly advantageous energy carrier, since it is the simplest, kind of carbon-containing compound, which is liquid at room temperature. Likewise, methane is an advantageous energy carrier, since a pronounced infrastructure exists for this hydrocarbon up to the ultimate consumer.

Various methods for producing methanol from atmospheric CO2 have already been proposed.

Weimer et al., Energy Conversion Management, 1996, volume 37, 1351 ff., generally discusses proposed solutions for the production of methanol using solar energy. One of the methods, introduced there generally and without concrete examples, comprises the steps of alkaline CO2 absorption, CO2 release, electrolytically obtaining hydrogen and methanol synthesis from the components, hydrogen and carbon dioxide. In this connection, it is proposed to use solar energy for covering the power required by the whole plant. This process, although suitable, is regarded as disadvantageous, since biomass is available as a better source of carbon and since the recovery of solar energy, among other things, is uneconomic, area-intensive and dependent on the weather. The problem of electrical energy, which is available only periodically, is not taken into consideration in this document.

Corbett et al., U.S. Pat. No. 4,339,547 discloses a similar process for obtaining fuels (hydrocarbons), comprising the steps of alkaline absorption of CO2, release of CO2, electrolytic recovery of hydrogen, methanol synthesis from the components, hydrogen and CO2, and conversion to hydrocarbons by means of a Fischer-Tropsch synthesis. This document discloses particularly advantageous equipment for absorbing the carbon dioxide.

Hardy et al., US 2005/02328833, also disclose a process for obtaining fuels (hydrocarbons), comprising the steps of alkaline CO2 absorption, CO2 release, electrolytic hydrogen recovery, methanol synthesis from the components, hydrogen and carbon dioxide, and the conversion to hydrocarbons by the Fischer-Tropsch synthesis. It is proposed in this document that the energy required be obtained by a nuclear reactor. It is an essential purpose of the whole plant, disclosed there, to use hydrocarbons, as fuel directly on board of a ship.

To summarize, it may be noted that the known processes, looked at as a whole, have different disadvantages, For example, some of the processes are unnecessarily complicated, some are not very environmentally friendly and, on the whole, not suitable for making an energy carrier available inexpensively and continuously. It is therefore an object of the present invention to eliminate one or more of the disadvantages of known plants.

The objectives, outlined above, are accomplished according to the independent claims. Advantageous embodiments are given in the specification and in the dependent claims. Further aspects of the invention are given in the dependent claims, as well as in the specification.

The invention accordingly is related to a power plant, not connected to the grid, for producing and storing combustible hydrocarbons, especially methanol, dimethyl ether and methane. The invention furthermore relates to a method for producing combustible hydrocarbons, to a floating body equipped with a power plant as described here, as well as to the use of the power plant or of the floating body for producing combustible hydrocarbons.

The general, preferred and particularly preferred embodiments, definitions and alternatives, listed in the following, can be combined in any way with one another and are an object of the present invention. Moreover, individual definitions/alternatives may be omitted.

Provided that another interpretation does not arise out of the direct context, the following concepts have the meanings given here:

The concept power plant generally describes a composite of different installations for producing energy. In stricter sense, this concept describes composite installations, which produce electrical energy and deliver it to an existing grid. Within the scope of the present invention, the concept, however, is to describe also such installations composites, which make available a chemical energy carrier (particularly methanol, methane and dimethyl ether. Such a power plant is not connected to a grid, if it has no direct connection to a consumer and, instead, stores the energy produced (or the energy carrier) and thus makes it available for delivery.

A floating body generally refers to any device, which can take up the parts of the installation named below and can float in regions of constant wind conditions or wave movement. In particular, this concept comprises all types of water vehicles, which can move under their own power ("mobile floating bodies", for example, motor ships by engine power or "sailing ships" by wind power) or must be moved (stationary floating bodies", such as "pontoons", "platforms" or "buoys"). According to the invention, the concept, "floating bodies moved by wind power" comprises conventional sailing ships equipped with mast and sail, as well as unconventional sailing ships, which use, for example, a hang glider or other technical devices. Furthermore, floating bodies can be constructed as single hull boats or multi-hull boats.

The concept "methanol synthesis" or "methanol production" relates to the formation of methanol from hydrogen and carbon dioxide or carbon monoxide. The following equations are given for the purpose of illustration:

$$CO_2 + 3H_2 \rightarrow H_3COH + H_2O$$

$$CO + 2H_2 \rightarrow H_3COH$$

The hydrogen required can also be formed in situ; this leads to the following empirical equation:

$$CO_2 + 2H_2O \rightarrow H_3COH + 3/2 O_2$$

The concept "methane synthesis" or "methane production" relates to the formation of methane from hydrogen and carbon dioxide or carbon monoxide. The following equations are given for the purpose of illustration:

$$4H_2O \rightarrow 4H_2 + 2O_2$$

$$CO_2 + 4H_2 \rightarrow CH_4 + 2H_2O\text{—resulting in the following empirical reaction:}$$

$$CO_2 + 2H_2O \rightarrow CH_4 + 2O_2$$

The concept "dimethyl ether (DME) synthesis" or "DME production" relates to the formation of DME from hydrogen and carbon dioxide or carbon monoxide. The following empirical equations are given for the purpose of illustration $$3CO = 3H_2 \rightarrow H_3C\text{—}O\text{—}CH_3 + CO_2$$

$$2CO_2 + 3H_2O \rightarrow H_3C\text{—}O\text{—}CH_3 + 3O_2$$

The chemical energy carriers (methanol, DME and methane), formed according to these reactions, may be present in different purities and do not have to be produced completely chemically pure, that is, the byproducts, impurities from preceding reaction steps and/or the starting material, etc. may be contained. The chemical energy carrier, made available according to the invention, is suitable, optionally after further purification steps, as an energy carrier in combustion motors or fuel cells or can be used as a starting material for chemical syntheses The invention furthermore is illustrated by the Figures.

Figure 2:
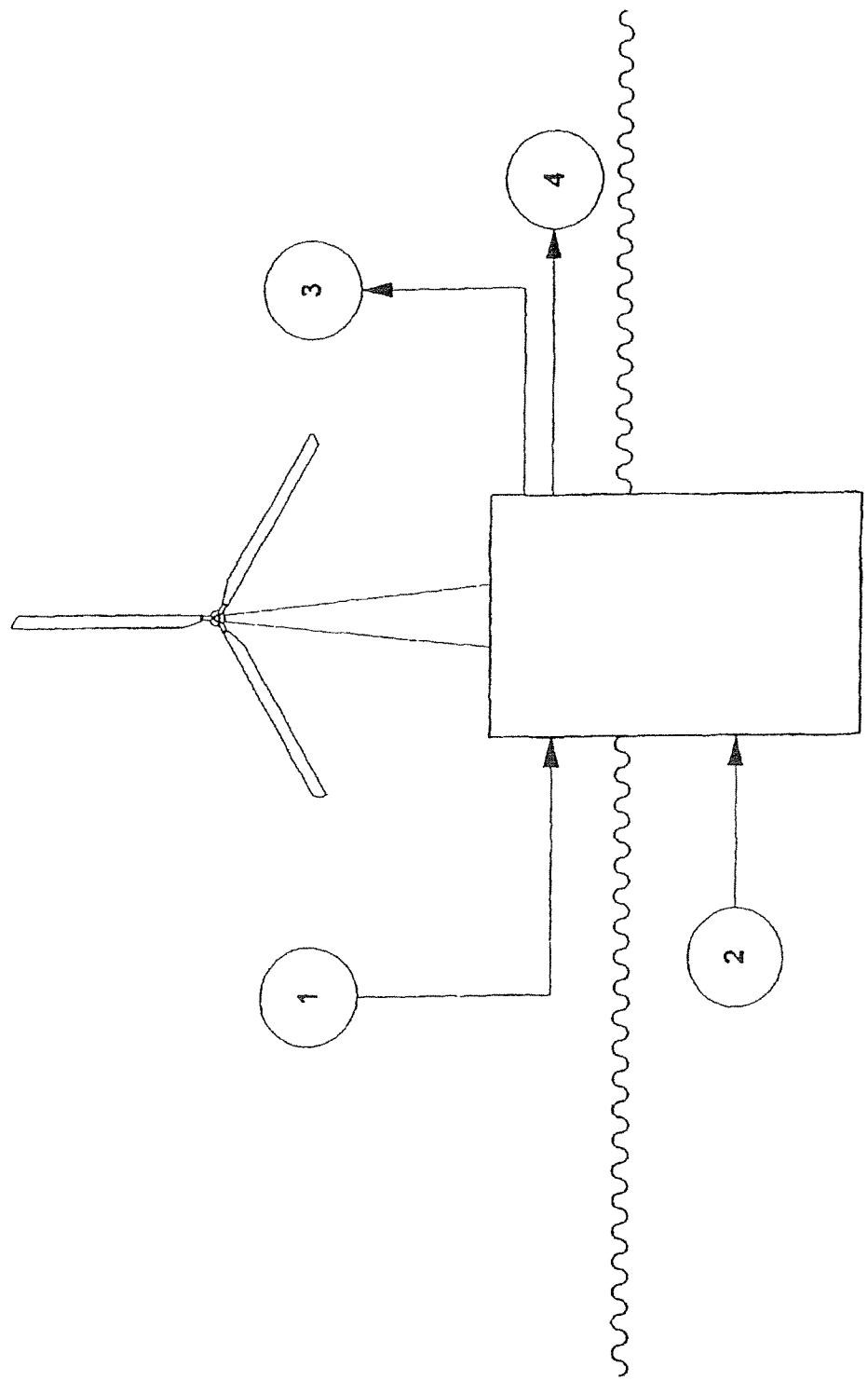
Figure 3:
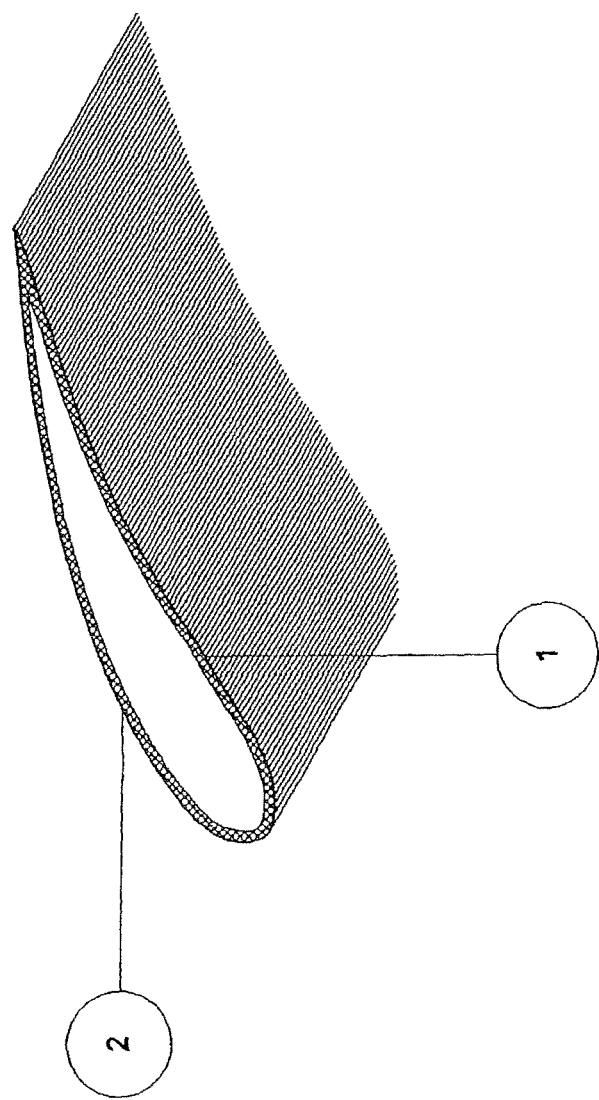

FIG. 1 shows a diagrammatic representation of an inventive power plant, the reference symbols having the following meanings:

Units
   A wind power plant or photovoltaic plant
   B $CO_2$ absorption plant
   C $CO_2$ desorption plant
   D $H_2$ synthesis plant
   E catalytic methanol synthesis plant
   F storage facility Material Flows
   1 air with a high $CO_2$ content
   2 air with a low $CO_2$ content
   3 unsaturated washing liquor
   4 saturated washing liquor
   5 $CO_2$
   6 $H_2O$
   7 $O_2$
   8 $H_2$
   9 methanol
   10 $H_2O$ FIG. 2 shows a diagrammatic representation of an inventive floating body containing at power plant for methanol production, the symbols having the following meaning:
   1 air with a high $CO_2$ content
   2 $H_2O$.
   3 air with a low $CO_2$ content
   4 methanol FIG. 3 shows a particular configuration of the wind power plant, in which the wind power plant and the $CO_2$ absorption plant are combined with one another, in that the rotor blades of the wind power plant are provided with microporous membranes for the absorption of $CO_2$. 1 shows the wash liquor with a low $CO_2$ content running forward and 2 shows the wash liquor with a high $CO_2$ content running back.

In a first aspect, the invention therefore relates to a power plant, which is not connected to the grid and is characterized in that it contains the following installation modules, the capacities of which are matched to one another: a) wind power plant, water power plant, solar thermal plant and/or photovoltaic plant for generating electrical energy for operating plants b) to f); b) $CO_2$ absorption installation for absorbing atmospheric $CO_2$; $CO_2$ desorption installation for the desorbing the $CO_2$ obtained in b); d) electrochemical or solar thermal $H_2$ synthesis installation for operating plant e); synthesis installation selected from the group comprising the catalytic synthesis of methanol, the catalytic synthesis of DME and the catalytic synthesis of methane; f) a storage installation selected from the group of methanol storage installation, DME storage installation and methane storage installation.

Such a power plant offers the possibility of harvesting and storing the energy in wind power, water power and/or sun energy almost completely independently of site. As a result, a large potential of possible locations is opened up. The chemical energy carrier (that is, the storage medium methanol, DME or methane) is synthesized here from its combustion products ($CO_2$ and $H_2O$) and thus forms a closed material cycle.

Methanol is an energy carrier with a comparatively high energy density, which is easily handled and can be stored for a prolonged period. Furthermore, the methanol, form pursuant to the invention, can be integrated without the difficulty into the existing energy supply system, used as a chemical raw material or employed directly in fuel cells (such as DMFC cells). DME and methane are also energy carriers with a comparatively high energy density, which can be handled and stored easily. Furthermore, the chemical energy carriers, which have been formed pursuant to the invention, can be integrated easily into existing energy supply systems, used as a chemical raw material or employed directly in fuel cell with out difficulty.

In contrast to known wind power, water power or photovoltaic installations, which are integrated in existing grids, no grid control problems arise, since there are no peak loads or downtimes, which have to be equalized. Rather, it is possible to bring about grid equalization by converting the chemical energy carrier formed into electrical energy.

In particular, the invention relates to the special matching of the synthesis technology to the output of the wind power, water power and/or photovoltaic installation: the functional integration of components of the synthesis installation into the wind power, water and/or photovoltaic installation and the specific selection and configuration of the individual installations.

The invention is to be explained further in the following and advantageous embodiments are to be shown.

In general: It is self-evident that the dimensions of the individual installations/modules a) to f) must be matched to one another. Such a design falls within the routine activities of an engineer. Furthermore, from a process, safety or production point of view, it may prove to be advantageous to construct installations a) to f) repeatedly. For example, it may be advantageous to provide several wind power installations, several synthesis installations and several storage installations. Such variations are within the scope of usual engineering activities and are included by the present invention. Furthermore, the individual elements of the installation may have to be adapted to conditions at sea. Such adaptations are already known from adjoining fields, for example, in conjunction with oil drilling platforms, on which further processing of the crude oil also takes place, or on tankers, which transport dangerous materials such as natural gas, $H_2O_2$, $H_2SO_4$ and the like.

Combination of installations/modules: As explained below even further, the installations a) to f) can also be constructed as combined installations. Accordingly, the wind power installation (a), by a special design, can also take over partly or completely the function of the CO2 absorption installation (b). Furthermore, the electrochemical hydrogen synthesis installation (d) and the catalytic methanol synthesis installation (e) may also be combined or constructed in the form of a reverse direct methanol fuel cell (DMFC). Moreover, the CO2 desorption installation (c) and the electrochemical hydrogen synthesis installation (d) may be combined with one another. The CO2 absorption installation and CO2 desorption installation may also be combined or coupled functionally. Such combined or integrated installations are included by the present invention.

Furthermore, for the optimum material and energy coupling of the installation, it may be meaningful to combine certain embodiments of the individual installations a) to f) with one another. Accordingly, for example, it is advantageous to combine a thermal CO2 desorption installation with a solar thermal hydrogen synthesis installation. Furthermore, it is advantageous, for example, to combine a CO2 desorption installation, which works according to the principle of reductive alkaline low-pressure electrolysis, with a methanol synthesis installation based on synthesis gas. Moreover, it is advantageous, for example, to combine the CO2 desorption installation, which works according to the principle of chlorination, with a hydrogen synthesis installation, which works according to the principle of chloroalkali electrolysis. In principle, the modules below may be combined in any way with one another. For example, for economic or technical reasons, particularly preferred combination arises, which are the object of the present invention. An overview of these combination is shown at the end of this specification by means of the morphological box. The individual installations named are described in detail below.

Floating body: The concept was already explained above. Floating bodies can be produced specifically for the inventive purpose. Alternatively, existing equipment can be changed over, for example, in that freighters or drilling platforms are equipped with appropriate installations. Freighters and buoys, for example, are suitable floating bodies.

Installation for producing energy (module a): for the process described here, electrical and/or thermal energy is required depending on the configuration. This energy is made available by a primary installation. In principle, all known installations, which make electrical or thermal energy available, are suitable. Wind power installations, water power installations, photovoltaic installations and solar thermal installations may be named as advantageous installations, wind power installations and solar thermal installations being particularly emphasized. Furthermore, water power installations are emphasized especially.

In connection with the present invention, all installations, which can convert wind energy into electrical energy, are to be understood as wind power installations ("WKA"), (module a1). Typically, wind power installations have a rotor, comprising a hub and rotor blades, which is mounted on a mast and coupled to a generator; accordingly, the concept comprises wind power installations with rotor blades revolving vertically or horizontally. Furthermore, wind power installations can be used with or without gear support.

In connection with the present invention, all installations, which can make use of the kinetic energy of the water or make use of the motion of floating bodies relative to water, are understood to be water power installations (module a2). A moved floating body ("sailing ship"), which is moved through essentially still water, would therefore also be preferred. Furthermore, a floating body, which can convert the energy of water waves into electrical energy, is also preferred.

In connection with the present invention, all installations, which can convert energy, contained in solar radiation, directly into electric energy, are understood to be photovoltaic installations (module a3).

In connection with the present invention, all installations, which can make thermal use of the radiation energy of the sun, are understood to be solar thermal installations (module a4).

The installations (modules), named above, are known as such and are commercially available or can be designed and manufactured according to known methods.

A vertically rotating wind power plant without gear support is used in one advantageous embodiment, which has the advantage that the wind power plant requires particularly little maintenance and can be installed without problems.

A horizontally rotating wind power plant with gear support is used in an alternative embodiment, which has the advantage that a particularly energy efficient and flexible wind power plant is used.

A solar thermal installation and, optionally, a wind power installation are used in a further alternative embodiment, which is of advantage if the downstream installation requires little electrical energy and much thermal energy.

A wave power machine of the "Pelamis" or "OPT Powerbuoy" type, which makes use of the up-and-down movement of the waves for converting the resulting energy into electrical energy, is used in a further, alternative embodiment of the invention. Such wave power machines are either anchored or positioned with other means, such as sails. Accordingly, a sailboat, to which OPT Powerbuoys are attached, is a specific embodiment of the above-mentioned water power installation A turbine, for example, as used in tidal power plants, which makes use of a flow in the water or an ocean flow, is a further alternative embodiment of the invention. Such turbines may be fastened, for example, to stationary floating bodies. The invention therefore also relates to a modular power plant, for which the floating body is stationary and which has a turbine disposed in the water.

In a further, alternative embodiment, a turbine is used, which is disposed in the water and fastened to the hull of a sailboat. In this embodiment, said sailboat is moved by wind power relative to the water and this drives the turbine for producing electrical power. Said sailboat may either be a classical sailboat with one or more hulls or a boat, which is equipped with unconventional devices for wind propulsion, such as a kite. The invention therefore also relates to a modular power plant, for which the floating body is a sailboat, which has one or more turbines disposed in the water.

CO2 absorption installation (module b): Numerous installations and processes are known for absorbing atmospheric carbon dioxide. According to the invention, CO2 absorption installations comprise installations based on a wash liquor (wet chemical installations, module b1) or not based on the use of wash liquors ("dry chemical installations", module b2).

Module b1: Within the scope of the present invention, those installations are preferred, for which the air (which contains approximately 350 ppm of CO2) is brought into contact with a wash liquor, especially an aqueous, alkaline, solution, preferably an alkali hydroxide such as NaOH or KOH, carbonate and/or hydrogen carbonate being formed (refer to Weimer et al., Energy Convers., Mgnt, 1996, page 1351 ff., which is taken up in this specification by reference (particularly Chapter 3.3.2). The CO2 from 1700 m$^3$ of air is required to produce 1 L of methanol. In order to supply a synthesis installation with a primary output of 600 KW with CO2, 12,000 m$^3$ of air must be supplied to the absorption installation per hour. Suitable wash liquors react reversibly with CO2 and are generally known; by way of example, the already mentioned sodium hydroxide solution is named. The reaction may take place, for example, according to the following equations in the aqueous medium:

$$2NaOH+CO2 \rightarrow Na2CO3+H2O$$

$$NaOH+CO2 \rightarrow NaHCO3,$$

the carbonate and hydrogen carbonate being in equilibrium with one another. If carbonate is concentrated on as a reaction partner in connection with the present invention, the corresponding reaction of the hydrogen carbonate is included and not shown here merely for reasons of clarity.

In one embodiment, the absorption can take place in open contact in a scrubbing tower provided with a filler. The air current initially is optionally moistened in this tower packed with filler and then passed through it countercurrently to the alkaline washing liquor.

In a further, advantageous embodiment, the absorption installation is of the Venturi tower type. Such Venturi towers contain means for applying the aqueous, alkaline solution, means for droplet formation/fogging this solution in the upper region of the tower and means for discharging the carbonate/hydrogen carbonate solution formed in the low region of the tower. Suitable Venturi towers are known from U.S. Pat. No. 4,339,547, which is taken up in this specification by reference (particularly FIG. 3a; b; column 2, line 63 to column 3, line 38).

In a further advantageous embodiment, the absorption installation contains microporous hollow fiber membranes, particularly hydrophobic, microporous, hollow fiber membranes, which contain the alkaline absorption liquid and are brought into contact with an air stream, in order to absorb atmospheric CO2 in this way. Such membranes are known and obtainable commercially, for example, from Hoechst-Celanese. The construction and dimensioning of appropriate absorbers is known and described, for example, in Stucki et al., in J. Hydrogen Energy, 1995, page 653 ff. This document (particularly page 656, "Experimental") is taken up in this specification by reference. In an advantageous embodiment, these microporous hollow fiber membranes are covered with a hygroscopic material, such as magnesium sulfate. This measure reduces the evaporation of the circulating water of the wash liquor.

In a known, special embodiment, the wind power installation and the CO2 absorption installation are combined with one another in that the rotor blades and/or the mast of the wind power installation is provided with the microporous membranes mentioned above. These membranes are mounted in such a manner on the mast and/or rotor blade, that, on the one hand, they are in direct contact with the air and, on the other, the washing liquor can circulate to and from the CO2 desorption installation. The invention therefore also relates to wind power plants and power plants connected to the grid, as described here, for which the rotor blades and/or the mast is/are provided with a hydrophobic, microporous membrane for CO2 absorption.

In a further advantageous development of the wet chemical absorption installations described here, an evaporation-reducing component is added to the washing liquor. Suitable components have a vapor pressure-reducing effect. Such components are known and magnesium sulfate is named as a specific example. The concentration of such components, required for them to be effective, depends on the construction of the installation, the raw materials used and the operating conditions. Suitable operating parameters can be determined by means of appropriate experiments; as a guiding point, 0.1 to 10% by weight of magnesium sulfate in the washing liquor is suitable.

Module b2: within the scope of the present invention, such installations are furthermore preferred, for which the air is contacted with solid calcium oxide at comparatively low temperature (particularly temperatures below 100° C., calcium carbonate being formed. The calcium oxide named preferably is present in a finely divided form, for example, as nanoparticles. Appropriate equipment and installations, which absorb gases by means of a solid absorber, are known and can be designed according to known methods. This dry chemical installation preferably is combined with the dry chemical CO2 desorption installation named below.

CO2 desorption installation (module c): installations for releasing CO2 from washing liquors, especially from carbonate-containing aqueous washing liquors, are generally known (module c1). Installations for releasing CO2 from solids, especially from carbonate-containing solids, are also generally known (module c2). Such a release can take place by physico-chemical, electrochemical or chemical means and is closely related to the compounds formed by the CO2 absorption.

In one embodiment, the CO2 is released by electrochemical means by electrolysis of the carbonate solution formed in an electrochemical membrane cell with formation of CO2 and hydrogen ("alkaline low-pressure electrolysis", module c11). Such cells are known; essentially, the reaction can be described by the following equation:

$$Na2CO3+4H2O \rightarrow 3H2+3/2O2+CO2+2NaOH$$

The advantage of this embodiment lies therein that the CO2 desorption installation and the hydrogen synthesis installation are combined with one another.

In an alternative embodiment, the carbon dioxide is released by electrochemical means by electrolysis of the carbonate solution formed in an electrochemical membrane cell with the formation of carbon monoxide (or by using a solid oxide electrolysis cell, SOEC, module c12). In conjunction with the present invention, such an installation is also considered as a CO2 desorption installation, since the CO2, bound from the air, is emitted once again, in the special case in the form of CO+½O2. Such cells are known; essentially, the reaction can be described by the following equation:

$$Na_2CO_3 + H_2O \rightarrow \tfrac{1}{2}O_2 + CO + 2NaOH$$

The advantage of this embodiment lies therein that carbon monoxide is formed, which is converted in the following methanol synthesis installation into methanol or in a DME synthesis installation into the DME, without forming water as byproduct. Furthermore, comparatively less power is required for this reaction.

In an alternative embodiment, CO2 is released chemically by acidification of the wash liquor from installation b) with optional subsequent electrodialysis (module c13). Desorption by the addition of an acid, such as aqueous sulfuric acid, is generally known and can be accomplished in common equipment, such as a stirred reactor. The salt formed in this reaction can be worked up once again in a subsequent electrodialysis. Essentially, the reaction can be described by the following equation:

$$Na_2CO_3 + H_2SO_4 \rightarrow Na_2SO_4 + CO_2 + H_2O$$

$$Na_2SO_4 + H_2O \rightarrow NaOH + H_2SO_4$$

The advantage of this method lies in the simple and certain CO2 desorption.

In an alternative embodiment, the CO2 is released by physicochemical (thermal) means by calcining (module c2). For this, an alkaline (earth) carbonate, preferably calcium carbonate, is heated until CO2 is split off. Suitable reactors for this reaction are known, such as rotary kilns or fluidized bed reactors. The alkaline (earth) carbonates required can be obtained directly from the CO2 absorption installation (by wet chemical or dry chemical means) or by reaction with Na2CO3 (from the absorption installations. The metal oxides, formed by the calcining, can be recycled by reaction with water (for the wet chemical method) or recycled without a further chemical reaction (for the dry chemical method). Essentially, the reaction for the wet chemical method can be described by the following equations, which summarize the preparation of the carbonate, the calcining and the recycling:

$$Na_2CO_3 Ca(OH)_2 \rightarrow CaCO_3 + 2NaOH$$

$$CaCO_3 \rightarrow CaO + CO_2$$

$$CaO + H_2O \rightarrow Ca(OH)_2$$

It is an advantage of this embodiment that a particularly finely divided carbonate is made available for the further reaction sequence. It is a further advantage of this embodiment that the reaction can be carried out without electrical energy.

Essentially, the reaction of the dry chemical method can be described by the following equations, which summarize the preparation of the carbonate and the recycling:

$$CaO(s) + CO_2(g) \rightarrow CaCO_3(s)$$

$$CaCO_3(s) \rightarrow CaO(s) + CO_2(g)$$

The solids of the above reactions are present in finely divided form, preferably as nanoparticles.

In an alternative embodiment of module c2, the CO2 is released from the CaCO3 in solar thermal installations at 500° to 2000° C. and preferably at about 1000° C. Solar thermal installations are known; in principle, all such installations are suitable, which produce the desired temperature by bundling or focusing, for example, by means of parabolic mirrors or Fresnel lenses.

In a further development of module c2, the partial pressure of the CO2 can be reduced in the reaction space in order to have a favorable effect on the release. A decrease in the partial pressure of CO2 is possible, for example, in that hydrogen is passed into the reaction space.

In an alternative embodiment, the carbon dioxide is released chemically by reacting the carbonate solution with chlorine ("Desorption by chlorination", module c14), optionally in the presence of a catalyst with formation of a chloride/hypochlorite solution and CO2. This reaction and appropriate equipment ("stripping towers") are known. The required chlorine is recycled electro-chemically, for example, in that the chloride/hypochlorite formed initially is reduced and subsequently supplied to the hydrogen synthesis installation, in which a chlorine alkali electrolysis is carried out. Essentially, the reaction can be described by the following equations, which summarize the desorption, the reduction and the hydrogen and chlorine synthesis:

$$Na_2CO_3 + Cl_2 \rightarrow NaCl + NaOCl + CO_2$$

$$NaOCl + NaCl \rightarrow 2NaCl + \tfrac{1}{2}O_2$$

$$2NaCl + 2H_2O \rightarrow 2NaOH + Cl_2 + H_2$$

Such an embodiment is indicated when the hydrogen synthesis installation is configured so that chlorine is produced as a byproduct.

In an alternative embodiment, the CO2 is released physicochemically in an installation by reducing the pressure ("degassing installation"). Such degassing installations are known. The advantage of this embodiment is that a technically simple and robust installation can be made available. This embodiment is advantageous especially when a washing liquor, which enters predominately into such physical bonding or weak chemical bonding with the CO2, that is, undergoes essentially absorption or coordination effects, is used in the CO2 absorption installation.

Hydrogen synthesis installation (module d): The necessary hydrogen can be made available by electrochemical (module d1) and/or solar thermal (module d2) means, electrochemical hydrogen synthesis plants being preferred. In principle, all known electrochemical cells, which electrolyze aqueous solutions with the formation of hydrogen, are suitable. Such cells are known, have been investigated extensively and can be designed by someone of ordinary skill in the art and integrated into the process as a whole. It is meaningful and necessary to adapt them, for example, to the preceding CO2 desorption installation. Moreover, in principle, all known solar thermal processes are suitable, which lead to the release of hydrogen. Here also, adaptation to other installations is meaningful and necessary. Furthermore, the operational safety, investment costs and efficiency are important parameters for all of hydrogen synthesis plants.

Module d1: In an advantageous embodiment, hydrogen is produced by means of PEM electrolysis (proton exchange membrane). This technology is state of the art and can easily be realized on the scale required.

In a further advantageous embodiment, hydrogen is produced by means of chlorine alkali electrolysis of an aqueous sodium chloride solution. In principle, all electrolysis cells, known for this purpose, are suitable. This embodiment is particularly advantageous if the CO2 desorption takes place by chlorination.

In a further advantageous embodiment, hydrogen is produced by means of high-temperature electrolysis of water with formation of hydrogen and oxygen. In principle, all electrolysis cells, known for this purpose, are suitable.

Advantageously, the water used is initially desalinated, for example, by means of an ion exchanger or by distillation. This embodiment is particularly advantageous if the CO2 desorption is not carried out by chlorination.

In a further advantageous embodiment, the aqueous carbonate/hydrogen carbonate solution, formed by absorption of carbon dioxide, is supplied directly to an electrolysis cell, CO2 and O2 being formed at the anode and hydrogen at the cathode and a hydroxide-containing solution resulting, which can be recycled for CO2 absorption ("alkaline low pressure electrolysis"). Such electrolysis cells are known and described in U.S. Pat. No. 3,135,673, the contents of which are taken up in this specification by reference. Essentially, the reaction can be described by the following equation:

$$Na_2CO_3 + 4H_2O \rightarrow 3H_2 + 3/2O_2 + CO_2 + NaOH.$$

This electrolysis cell can advantageously be constructed so that, in a three-part cell, separated by diaphragms, hydrogen and O2 can be removed from the cathode and anode spaces and the CO2 formed can be removed from the region in between.

Module d2: In a further, advantageous embodiment, the necessary hydrogen is produced by solar thermal processes without electricity. This can be accomplished, for example, by the thermal dissociation of zinc oxide at temperatures above 2000° K, zinc and O2 being formed. The zinc reacts with water with the formation of zinc oxide and hydrogen, which is released. This embodiment is advantageous if solar radiation of high intensity is available. Advantageously, such a solar thermal hydrogen synthesis installation can be combined with a CO2 desorption installation, which releases the CO2 because of thermal processes, as described above. In this embodiment variation, the reaction energy, required for all endothermic processes, is made available thermally. Thermal energy is made available for the CO2 desorption and the hydrogen synthesis; the CO2 absorption and the synthesis of methanol, DME and methane are exothermic reactions. The low electrical energy required and the high overall efficiency of the power plant would seem to be a particular advantage of this embodiment. Correspondingly, such a power plant could be installed advantageously in regions with high solar radiation, for example, in desert regions.

Synthesis installation for producing combustible hydrocarbons (module e). The synthesis of combustible hydrocarbons, especially of methanol, methane and DME, as well as appropriate installations are known in the prior art. Advantageously, installations are used which are based on catalytic synthetic processes.

Methanol synthesis installation (module e1): As already stated, the present invention includes methanol synthesis installation which convert either i) carbon dioxide (CO2) and hydrogen or ii) carbon monoxide (CO) and hydrogen or iii) carbon dioxide and water into methanol. These installations can be designed so that a practically complete conversion to methanol takes place by a simple throughput. Alternatively, these installations can also be designed or operated so that only a partial reaction of the CO or CO2 used takes place. In this case, unreacted starting material is either recycled after removal of the products (methanol) or (especially in the case of CO2) discharged into the environment. Preferably, recycling, without discharge into the environment, takes place completely or practically completely.

In an advantageous embodiment, methanol is synthesized from the component, CO2 and hydrogen. Installations for reacting CO2 and hydrogen to form methanol are generally known. Typically, these installations are designed so that the reaction in the reactor takes place at 50 to 100 bar and 200° to 300° C. The reactors may be designed as solid bed or fluidized bed reactors. Copper-doped solid catalysts, for example, are suitable catalysts. The methanol synthesis can be carried out in one or more steps. This reaction can be illustrated by the following reaction equation:

$$CO_2 + 3H_3 \rightarrow H_3COH + H_2O$$

This variation is particularly advantageous, since such commercially obtainable installation can be dimensioned so that they match the electrical energy made available by typical wind power plants. Advantageously, a distillation unit, which enables the water formed to be separated partly or completely from the methanol, is provided in this installation. The invention accordingly relates also to a power plant as described here, for which the methanol synthesis installation has a copper-containing catalyst (for reacting CO2 and hydrogen) and to which optionally a distillation unit (for the partial or complete separation of the methanol produced and for the recycling of the water to the electrolysis), is assigned.

In a further advantageous embodiment variation, the methanol is synthesized from synthesis gas (a gaseous mixture containing essentially carbon monoxide and hydrogen, preferably in the molar ratio of 1:2). Installations for reacting carbon monoxide and hydrogen to form methanol are generally known. This conversion can be illustrated by the following reaction equation:

$$CO + 2H_2 \rightarrow H_3COH$$

In conjunction with the present invention, such installations are referred to as "methanol/synthesis gas installations". For this variation, it is advantageous that water is not formed as a byproduct, so that it is not necessary to separate water from the methanol. For this embodiment, however, it is necessary initially to reduce the CO2 from the air to carbon monoxide. Appropriate processes and installations are known and can be integrated in the power plant described here.

In one variation, the methanol/synthesis gas installation contains a unit for the high-temperature electrolysis of CO2. Advantageously, such units contain a solid electrolyte, which conducts oxygen ions, such as ZrO/Y2O3. Typical reaction temperatures are between 800° and 1000° C. The CO2/H2O mixtures, supplied to the unit, are reduced in accordance with the equations below by applying a voltage:

$$CO_2 \rightarrow CO + \tfrac{1}{2}O_2$$

$$H_2O \rightarrow 2H_2 + O_2.$$

The stoichiometry of the synthesis gas produced is dependent on the voltage applied, the contact time, the residence duration and the temperature and can be optimized in a simple series of experiments. If such a high-temperature electrolysis is combined with the methanol synthesis installation, it is possible to do without a separate hydrogen synthesis installation depending on the operating point of the high-temperature electrolysis unit.

In a further variation, the methanol/synthesis gas installation is combined with an installation for the reductive, alkaline, low-pressure electrolysis. This installation makes the CO required available.

In a further, preferred embodiment, the methanol synthesis takes place according to the following equation:

$$CO_2 + 2H_2O \rightarrow H_3COH + 3/2O_2.$$

This installation is referred to as a "direct methanol installation". This method is particularly advantageous since the components and CO2 and water can be used directly. Accordingly, for this variation, methanol and hydrogen synthesis installation (installation d) and e)) are combined in a single installation. Such installations are known and described, for example, in U.S. Pat. No. 5,928,806, the contents of which are taken up in the specification by reference.

Methane synthesis installation (module e2): In one embodiment, methane is synthesized from the component CO2 and hydrogen. Installations for converting CO2 and hydrogen to methane are generally known. Typically, these installations are designed so that the conversion takes place in the reactor at 1 to 30 bar and preferably at atmospheric pressure and at a temperature of 300° to 400° C. The reactors may be designed as solid bed or fluidized bed reactors. Nickel-doped solid catalysts, for example, are suitable. The synthesis of methanol can be carried out in one or several steps, preferably in one step. This conversion can be illustrated by the following reaction equation:

$$CO2+4H2 \rightarrow CH4+2H2O$$

This variation is particularly advantageous, since it can be miniaturized easily; a pressureless variation of the method is already known and purification by distillation can be omitted. These advantages can eliminate partly or completely the disadvantage of storing under pressure.

The invention accordingly also relates to a power plant, as described here, for which the methane synthesis installation contains a nickel-containing catalyst (for the conversion of CO2 and hydrogen), and which does not require a distillation unit for separating the product.

Dimethyl ether synthesis installation (module e3): In one embodiment, DME is synthesized from methanol with the splitting off of water. Installations for this conversion are generally known. Typically, these installations are designed so that the reaction takes place in the reactor at 30 to 80 bar and preferably at 50 bar and at a temperature of 200° to 300° C. The reactors may be designed as solid bed or fluidized bed reactors. Copper/iron-doped solid catalysts, for example, are suitable. This variation is particularly advantageous since, with DME, an energy carrier is produced, which can be liquefied under a low pressure.

Alternatively, DME can be synthesized directly; appropriate installations and catalysts are known. The empirical equations of such reactions are given below:

$$3CO+3H2 \rightarrow H3C-O-CH3+CO2$$

$$2CO2+3H2O \rightarrow H3C-O-CH3+3O2$$

Storage installation (module f): Storage installations for liquid or gaseous, combustible hydrocarbons are known.

Methanol storage installation (module f1): Storage installations ("tanks") suitable for methanol are known. Because of its physicochemical properties, especially the flash point, vapor pressure and dissolving properties, tanks must consist of suitable materials and have appropriate safety devices. Such materials and safety devices are known to those of ordinary skill in the art. Furthermore, provisions can be made so that the methanol storage installation is separated spatially from the other parts of the installation. The invention therefore also relates to a floating body, as described here, consisting of two individual devices, which are connected to one another. One of the devices contains installation f) and the second device contains the installations a) to e).

Methane storage installation (module f2): Installations for storing methane preferably are designed so that either gaseous methane is stored at 200 bar ("CNG") at ambient temperature or gaseous methane is stored under no pressure and at ambient temperature or liquid methane is stored under no pressure at −163° C. ("LNG"). Appropriate installations are already in use on a large industrial scale. As for the rest, the statements made for methanol apply correspondingly.

DME storage facility (module f3): The statements, made for methanol, apply correspondingly also for DME. DME can be stored like LPG so that the appropriate installations of this invention can be used. Preferably, the DME storage facility is designed so that liquid DME is stored at 5 bar and ambient temperature.

In an advantageous embodiment, the present invention therefore also relates to a water vehicle, as described here, consisting of a composite of two or more individual water vehicles, characterized in that a first water vehicle contains the installations a) to e) and the therewith connected further water vehicles each contain a storage installation f). In this embodiment, the operating safety is increased and the flexibility of the whole installation is improved as well.

In a further advantageous embodiment, the methanol storage installation is separated by a movable partition (for example, a membrane) into two partial volumes. Accordingly, it is possible to store water in the installation, the water being required in the course of the reaction. The volume of the water consumed corresponds approximately to the volume of the methanol formed. By means of this measure, it is possible to do without a local water preparation installation. Furthermore, with a suitable arrangement of the storage installation on a floating body, this embodiment leads to increased stability.

Secondary installations: aside from these necessary installations, the floating body may contain further installations ("secondary installations" or modules). These comprise those installations, which are suitable for purifying starting materials, for making available and recovering auxiliary materials and for recovering energy, especially thermal energy. Furthermore, interim storage facilities for intermediate products may be provided, such as batteries for the interim storage of electric energy, gas tanks for the interim storage of CO2 and hydrogen and liquid tanks for the interim storage of auxiliary materials. Likewise, installations for the regeneration of the catalysts and the electrolysis cells may be provided. Furthermore, storage for the optionally produced oxygen may be provided. These secondary installations are known and can be designed appropriately by someone of ordinary skill in the art.

Scaling: The scaling of an inventive power plant depends on various parameters and is not limited by the invention. Typically, the available wind power or solar energy and the installations known for these represent an upper limit. The size of the inventive power plant is characterized suitably by stating the primary electrical energy produced (by wind power or solar energy), since the further installations are matched to these. For example, for large installations, a single wind power installation with approximately 10 MW may be mentioned as the upper output limit. The further components are to be designed for this output. Typically, the size of the installations d) to e) represent a lower limit, since, below a critical size, the installations are too small to be operated efficiently. In combination with a direct methanol fuel cell, approximately 100 W would be mentioned as the lower output limit. The remaining installations are to be designed appropriately for this output. Accordingly, the invention relates to a power plant, which is not connected to the grid, and has an output of 100 W to 10 MW, preferably of 1 kW to 5 MW and particularly of 0.5 to 3 MW.

In particular, the invention also relates to a power plant, which is positioned preferably at places with constant wind conditions or suitably flowing water or suitable wave motions of the water (as described below). This positioning solves many of the problems of existing power plants (in the case of land-bound installations, especially noise and natural scenery), in the case of offshore installations, especially the costs of foundations, maintenance and connections to the grid) or of water power installations.

Accordingly, for offshore installations that are not anchored, the possibility exists for the first time of producing an energy carrier, which (1) is stored in concentrated form, (ii) can be transported well and (iii) used in an existing infrastructure. For comparison, it is pointed out that, for hydrogen as energy carrier, there is no existing infrastructure and storage and transport are associated with appreciable technical problems.

In a second aspect, the present invention relates to a floating body, especially to a water vehicle, comprising the following installations: a) a wind power or water power installation for producing electrical energy for operating the installations b) to f); b) a CO2 absorption installation for absorbing atmospheric CO2; c) a CO2 desorption installation for the desorption of the CO2 obtained in b); d) an electrochemical hydrogen synthesis installation; e) a catalytic synthesis installation for producing combustible hydrocarbons and f) a storage installation for storing the hydrocarbons obtained in e). Such a floating body offers the possibility of producing and storing combustible hydrocarbons (such as methane, DME or methanol) from the practically unlimited resources of CO2 from the air and hydrogen from water by means of wind energy or water power. Since all the necessary resources are available at no cost, it is possible to produce these combustible hydrocarbons as valuable and environmentally friendly energy carriers inexpensively. Furthermore, the storage of such hydrocarbons on such a device is possible. The individual parts of the installation a) to f) are known and, on the basis of general expert knowledge, can be dimensioned and adapted to the requirements for the operation of a flexible device. Preferably, installations a) to f) are configured as described in this document.

Such a floating body can be installed remotely from the consumer, since there are neither performance losses due to transmission nor cost for the grid connection. This makes intercontinental transport of energy possible, for example, even from economic points of view. A basic concept of the present invention therefore is to "harvest" regenerative energy where it is available uniformly and in a high density, to convert the energy obtained into a chemical energy carrier, which is stored and then emptied discontinuously for further use.

Furthermore, such a floating body can easily be repositioned, for example, in order to carry out maintenance work or to operate in regions with optimum wind or wave or flow conditions.

In one embodiment, the invention therefore relates to a water vehicle as floating body, which is equipped with a wind power installation. In this embodiment, the axial resistance of the rotor can be used for propelling the floating body, in order to make the positioning or repositioning possible in this way or to support it.

In a further embodiment, the invention therefore relates to a buoy as floating body, which is equipped with a wind power installation.

In a further embodiment, the invention therefore relates to a sailboat as floating body, which is equipped with a water turbine.

In a third aspect, the present invention relates to a power plant or a floating body, which is not connected to the grid, as described here, especially a buoy or a water vehicle, for producing and storing combustible hydrocarbons such as methanol, methane and DME. The power plant is designed so that the production and the "interim" storage of combustible hydrocarbons is the essential or exclusive purpose. The floating body can be designed so that the production and the "interim" storage of combustible hydrocarbons is its essential or exclusive purpose. Likewise, it is possible that the installations are used as auxiliary units for driving the floating body or that the hydrocarbon produced is used in further processes. Preferably, the inventive floating body is used for the production and storage of combustible hydrocarbons, especially methane or methanol or DME.

In a fourth aspect, the invention relates to a method for the production of combustible hydrocarbons (especially methanol, methane and/or DME, the method comprising the steps of a) positioning a power plant or a floating body, as described here, in a region, which has constant wind conditions, constant wave movements or constant solar radiation; b) operating the installations of this power plant or floating body; and c) discontinuously or preferably periodically emptying the storage installation. This method makes it possible to produce a chemical energy carrier in a simple and safe manner and make it available flexibly as required. The individual steps are explained in the following.

Step a) Regions with constant wind conditions are generally known. The necessary strength of the wind depends on the design of the wind power installation. Typically, an average wind velocity of at least 7 m/s should exist. The wind conditions are considered to be constant if the average wind velocity is present at least 70% and preferably at least 80% of the time. Regions of the trade winds and regions which form a "natural jet", such a regions in the vicinity of the coast, regions between islands, at mountain passes and on peaks, etc. are typical regions. In general, it should be taken into consideration when positioning, that a constant wind increases the degree of utilization; a strong wind makes a high generator output possible with a small rotor area; if there is little vertical wind shear, wear is reduced and the output likewise is increased. These requirements are fulfilled particularly by trade winds and this represents a considerable advantage over land-bound installations.

Regions with constant wave motions are generally known. The required strength of the wave depends on the design of the wave power installation. Typically, the wave it should be less than 10 m high and preferably between 2 to 8 m. Wave conditions are considered to be constant if the average annual wave height is more than 0.7 m. The regions of the South Pacific are typical regions.

Regions with a constant solar radiation are also generally known. Regions, in which the average annual intensity of the solar radiation is more than 200 W per $m^2$ are regarded to be suitable. Typical regions are, for example, on the Arabian Peninsula or in Northern Africa.

The water vehicles can be positioned in various ways. In the simplest case, the water vehicle is anchored at the desired position. Alternatively, the water vehicle can tack, being kept on course by engine power and/or wind power, depending on the construction. In a further alternative, the water vehicle is repositioned at certain time intervals, for example, when the weather changes or because of seasonal fluctuations. The invention therefore also relates to a method, for which the positioning of the floating body optionally comprises a continuous or discontinuous repositioning.

In an advantageous embodiment, the resistance of the wind vehicle for driving the floating body, especially a ship, can be utilized partly or completely. The invention therefore also relates to a method, as described here, in which the floatable device is positioned and/or repositioned using the resistance of the wind power installation partly or completely.

The positioning of a vehicle, which is not installed on a floating body, relates essentially to the advantageous setting up of the wind power installation or solar thermal installation. Here also the aforementioned criteria can be employed.

Step b) The individual installations are operated in a known manner, depending on the design. The production capacity of the individual parts of the installation must be matched to one another. For example, the electric energy generated must be sufficient for all parts of the installation b) to f) as well as, if necessary, for any secondary units present. Furthermore, the production of hydrogen and the desorption of CO2 must be matched to one another. Furthermore, the installations can be designed so that a completely automatic, remotely monitored production is possible and/or that an operating crew is present on site. If the water vehicle is anchored, a fully automated operation is possible. If the water vehicle tacks, an at least partial manual operation is preferred, which monitors and controls at least the positioning of the water vehicle.

Step c) According to the invention, the storage installation is emptied discontinuously, preferably, at periodic intervals. As a parameter for these intervals, either a unit of time (such as a month, quarter or year) or the degree, to which the storage facility is filled (for example, at least up to 50% or no more than 90%) or a spatial parameter (for example, in that a water vehicle, tacking in trade winds, moves along a certain course) or a combination of the above can be used. In connection with the present invention, the concept of "periodic" is not to be understood in the exact mathematical context; rather, the chemical energy carrier produced is produced and stored on the floating device and delivered discontinuously to further consumers.

The following examples are intended to explain the invention further without limiting it.

EXAMPLE 1

Buoy with Rotor the floating body is equipped with the following installations:
a 600 kW wind power generator as module a
a blower-air moistener as module b; cross sectional area=9 m², v=3.5 m/s, open contact with aqueous sodium hydroxide solution in scrubbing tower
A sulfuric acid-containing regenerator for releasing the CO2 with connecting electrodialysis as module c;

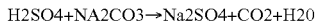
H2SO4+NA2CO3→Na2SO4+CO2+H20

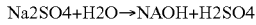
Na2SO4+H2O→NAOH+H2SO4 an electrolysis cell for the electrolysis of water as module D

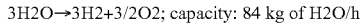
3H2O→3H2+3/2O2; capacity: 84 kg of H2O/h a methanol synthesis installation with a distillation unit as module e; capacity of 50 kg of methanol/h
a tank for holding the methanol formed as module f; capacity of 300 m³.

This power plant produces 50 kg of methanol/h, which corresponds to an energy content Hu of 274 kWh (efficiency of 46%). The sodium hydroxide and sulfuric acid components are recycled. CO2 and water are taken from the environment.

EXAMPLE 2

Wind Power Plant

A power plant with the following installations:
a combined module a and b is formed by a horizontal wind power installation with gears, the rotor blades of which are coated with an HF membrane
a sulfuric acid desorption installation with downstream electrodialysis as module c
a PEM electrolysis installation as module d
a methane synthesis installation without a distillation unit as module e
a CNG tank as module f Such a power plant may be installed, for example, on an island in the North Atlantic.

EXAMPLE 3

Sailing Ship a sailing ship is equipped with the following installations:
a turbine, mounted at the hull and lying in water as module a
a CO2 absorption installation with evaporation inhibitors; basically open contact, countercurrently, with fillers, as module b
a three-chamber electrolysis as combined modules c) and d)
a methanol synthesis installation with a distillation unit as module a
a methanol tank as module f)

Such a ship, can be operated, for example, by tacking in trade winds.

EXAMPLE 4

Strictly Thermal Power Plant

A power plant with the following modules
a dry CO2 absorption installation, which works with calcium oxide nanoparticles as module b)
a thermal calcium carbonate cracking installation, matching the CO2 absorption installation, with hydrogen superimposition as module c)
a thermal hydrogen synthesis installation according to the ZnO/H2O cycle as module d)
a methane synthesis installation without a distillation unit as module e
an LNG tank as module f)

Such a power plant may be installed, for example, on the Arabian Peninsula. As module a), a gas engine is provided, which uses the methane produced as fuel. In this embodiment, a module a is required only for supplying the auxiliary units.

EXAMPLE 5

Wave Power Plant

A ship is equipped with the modules b) to f), described below; several modules a) are connected with them
a wave power installation of the Pelami type as module a)
a wet chemical CO2 absorption installation, which uses uncoated HF membranes, as module b)
an SOEC installation as a combined module c) and d)
a DME synthesis installation without a distillation unit as module e)
an LPG tank as module f)

Such a power plant can be installed, for example, in the South Pacific.

The following morphological box combines the 5 examples mentioned as well as further configurations of the invention in an easily surveyed manner, without limiting this invention.

| O Position | landgebunden stationär / mobil | | | schwimmend stationär / mobil | | |
|---|---|---|---|---|---|---|
| A E-Erzeugung | A1 Windkraft — A11 Vertikal ohne Getriebe / A12 Vertikal mit Getriebe (Typ Vestas 650) | A4 Solarthermie — Thermoelektrisch (Typ Andasol) / Hoch-temp.thermie (Typ Parabolspiegel) | | A21 Wellenkraft — Wellenkraft elekritsch (Typ Ocean Power) | A22 Wasserstromung — Wasser bewegt (Gezeitenkraftwerk) / Kraftwerk bewegt (Typ Segelschiff mit Turbine) | A3 Photovoltaik |
| B Absorption | B1 Nasschemisch (NaOH, KOH) ohne Zusatzstoffe / mit Verdunstungsinhib. | | | | B2 Trockenchemisch (CaO) Nanopartikel | |
| C Desorption | C11 Dreikammerelektrolyse | C12 reduktive Desorption mittels SOEC | C13 H2SO4 Sauerung Na2SO4 Dialyse | C14 Chlorierung | C15 CaOH2 Basentausch dann C2 | C2 Therm. Spaltung von CaCO3 — ohne H2 Überlagerung / mit H2 Überlagerung |
| D Desorption | D1 elektrolytisch — Dreikammer-Elektrolyse / SOEC / PEM EC / Chloralkali-Elektrolyse | | | | D2 thermisch ZnO/H2O Zyklus | |
| E H2 Synthese | E1 CO2 zu Methanol / CO zu MeOH / RDMFC | | E3 MeOH zu DME / CO zu DME | | E2 CH4 Direktsynth. | |
| | mit Destillation | | ohne Destillation | | | |
| F KW Speicher | F1 Methanoltank | F3 DME Speicher Druck-tank, 5 bar Ballon | | | F2 CH4-Speicher Ballon / Druckbeh. 200 bar / LNG Tank | |

Key for Above Box

| | |
|---|---|
| Landgebunden | Land-bound |
| Stationär | Stationary |
| Mobil | Mobile |
| Schwimmend | Floating |
| A E-Erzeugung | Energy Generation |
| A1 | Wind power |
| A11 | Vertical without gears |
| A12 | Vertical with gears (Vestas 650 type) |
| A4 | Solar thermoelectric (Andasol type) high temperature thermal (parabolic mirror type) |
| A21 | Wave power wave power electric (ocean power type) |
| A22 | Water flow water moves (tidal power plant) Power plant moves (sailing ship type with turbine) |
| A3 | Photovoltaic |
| B Absorption | |
| B1 | Wet chemical (NaOH, KOH) without additives with evaporation inhibitor |
| B2 | Dry chemical (CaO) Nanoparticles |
| C Desorption | |
| C11 | three-chamber electrolysis |
| C12 | reductive desorption by means of SOEC |
| C13 | H2SO4 acidification |
| | Na2SO4 dialysis |
| C14 | Chlorination |
| C15 | CaOH2 base exchange then C2 |
| C2 | thermal splitting of CaCO3 without superimposing H2 thermal splitting of CaCO3 with superimposing H2 |
| D H2 synthesis | D1 electrolytic three-chamber electrolysis SOEC PEM EC chloroalkali electrolysis |
| | D2 thermal ZnO/H2O cycle |
| E hydrocarbon synthesis | E1 CO2 to methanol CO to methanol RDMFC |
| | E3 methanol to DME carbon monoxide to DME |
| | E2 Direct synthesis of methane |
| Mit Destillation | with distillation |
| Ohne Destillation | Without distillation |
| F hydrocarbon storage tank | F1 methanol tank |
| | F3 |

-continued

| Key for Above Box |
| --- |
| DME storage tank |
| 5 bar pressure tank |
| F2 |
| methane storage tank |
| balloon |
| pressurized container, 200 bar |
| LNG tank |

The invention claimed is:

1. A power plant, not connected to the grid, which is installed on a floating body and characterized in that it contains the following installations, the capacities of which are matched to one another:
   a) installation for producing electrical and/or thermal energy comprising a wind power installation for operating the installations of b) to f):
   b) CO2 absorption installation for absorbing atmospheric CO2, wherein rotor blades and/or masts of the wind power installations are provided with a hydrophobic microporous membrane for CO2 absorption;
   c) CO2 desorption installation for desorbing the CO2 obtained in b);
   d) electromechanical or solar thermal hydrogen synthesis installation for operating the installation e);
   e) synthesis installation selected from the group comprising catalytic methanol synthesis installations, catalytic dimethyl ether synthesis installations and catalytic methane synthesis installations; and
   f) storage tank installation from the group comprising methanol storage tank installations, dimethyl ether storage tank installations and methane take storage installations.

2. The power plant of claim 1, not connected to the grid, further comprising a second installation for producing electrical and/or thermal energy comprising a water power installation including a wave power machine or turbine, fastened to the floating body.

3. The power plane of claim 1, not connected to the grid, characterized in that air current in the CO2 absorption installation optionally is moistened initially and then brought into contact countercurrently with alkaline washing liquor.

4. The power plant of claim 1, not connected to the grid, wherein the hydrophobic microporous membranes are covered with a hygroscopic material.

5. The power plant of claim 1, not connected to the grid, characterized in that the CO2 desorption installation c) operates according to the principle of acidification, optionally with subsequent electrodialysis.

6. The power plant of claim 1, not connected to the grid, characterized in that the electromechanical hydrogen synthesis installation d) operates according to the principle of high-temperature electrolysis of water, which optionally is desalinated.

7. The power plant of claim 1, not connected to the grid, characterized in that the synthesis installation e) is either
   a) a methanol synthesis installation, which contains a copper-containing catalyst and that a distillation unit optionally is assigned to this installation or
   b) a methane synthesis installation, which contains a nickel-containing catalyst and that optionally a distillation unit is not assigned to this installation.

8. The power plant of claim 1, not connected to the grid, characterized in that the CO2 desorption installation c) produces carbon monoxide under reductive conditions from carbonate used and that the catalytic methanol synthesis installation e) is a methanol/synthesis gas installation.

9. The power plant of claim 1, not being connected to the grid, characterized in that the CO2 desorption installation c) works solar thermally according to the principle of calcinations and that the hydrogen synthesis installation d) is operated with a solar thermal process.

10. The power plant of claim 1, not connected to the grid, characterized in that the CO2 absorption installation contains a wet chemical CO2 absorption installation containing a washing liquor, wherein the washing liquor contains a component, which reduces evaporation.

11. The power plant of claim 1, not connected to the grid, characterized in that the CO2 absorption installation is a dry chemical CO2 absorption installation and the CO2 desorption installation is a dry chemical CO2 desorption installation.

12. A method, comprising:
   using the power plant of claim 1, not connected to the grid, to produce and store methanol, dimethyl ether and/or methane.

13. The power plant of claim 1, not connected to the grid, further comprising at least a second installation for producing electrical and/or thermal energy comprising a photovoltaic installation and/or a solar thermal installation.

* * * * *

UNITED STATES PATENT AND TRADEMARK OFFICE
CERTIFICATE OF CORRECTION

PATENT NO.        : 8,715,581 B2
APPLICATION NO. : 12/744104
DATED             : May 6, 2014
INVENTOR(S)       : Gregor Waldstein It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1018 days.

Signed and Sealed this

Twenty-ninth Day of September, 2015

Michelle K. Lee
*Director of the United States Patent and Trademark Office*